(12) United States Patent
Waldal et al.

(10) Patent No.: US 10,522,246 B2
(45) Date of Patent: Dec. 31, 2019

(54) CONCEPTS FOR EXTRACTING LAB DATA

(71) Applicant: OPTUM, INC., Minnetonka, MN (US)

(72) Inventors: Adam Waldal, Coon Rapids, MN (US); Robin Hillyard, Carlisle, MA (US)

(73) Assignee: OPTUM, INC., Minnetonka, MN (US)

( * ) Notice: Subject to any disclaimer, the term of this patent is extended or adjusted under 35 U.S.C. 154(b) by 557 days.

(21) Appl. No.: 14/724,959

(22) Filed: May 29, 2015

(65) Prior Publication Data
US 2016/0350483 A1    Dec. 1, 2016

(51) Int. Cl.
*G16H 10/60*    (2018.01)

(52) U.S. Cl.
CPC .................. *G16H 10/60* (2018.01)

(58) Field of Classification Search
CPC .... G06K 9/6203; G06F 19/322; G16H 10/60; G16H 10/10; G16H 50/50; G16H 10/40
USPC .............................................................. 705/3
See application file for complete search history.

(56) References Cited

U.S. PATENT DOCUMENTS

| | | | |
|---|---|---|---|
| 5,276,771 A * | 1/1994 | Manukian | G06K 9/627 706/17 |
| 5,664,109 A * | 9/1997 | Johnson | G06F 19/322 705/2 |
| 2003/0028401 A1 * | 2/2003 | Kaufman | G06Q 10/10 705/3 |
| 2009/0094059 A1 * | 4/2009 | Coleman | G06F 19/3456 705/3 |
| 2013/0036111 A2 * | 2/2013 | Kramer | G06F 16/583 707/723 |

OTHER PUBLICATIONS

U.S. Appl. No. 14/336,416, filed Jul. 21, 2014; In re: Stella, entitled *Targeted Optical Character Regonition(OCR) For Medical Terminology*.

* cited by examiner

*Primary Examiner* — Hiep V Nguyen
(74) *Attorney, Agent, or Firm* — Alston & Bird LLP

(57) ABSTRACT

Computer program products, methods, systems, apparatus, and computing entities for extracting lab result data from lab reports are provided. In one example embodiment, an example computing device receives a lab report. The computing device identifies one or more relevant portions of the lab report. The computing device then generates parsed lab report data from only the identified one or more relevant portions of the lab report. Subsequently, the computing device extracts patient information and lab results from the parsed lab report data. Using various embodiments of the present invention, patient information and lab results can be efficiently extracted for incorporation into structured data sets maintained, for example, by a healthcare company.

15 Claims, 6 Drawing Sheets

| LAB COMPANY LOGO ⌐302 | Lab Company Name ⌐304<br>1 Main Street<br>Springfield, State ZIP | Report Status: FINAL<br>DOE, JOHN |
|---|---|---|

⌐306

| Patient Information | Specimen Information | Provider Information |
|---|---|---|
| Name: John Doe<br>DOB: 1/1/1980<br>Age: 34<br>Fasting: Y<br>Gender: M<br>Phone: (800) 123-4567<br>Policy ID: 5555555 | Specimen #: 12345<br>Requisition #: 1234567<br><br>Collected: 1/1/2014 10:00 EDT<br>Received: 1/1/2014 15:22 EDT<br>Reported: 1/2/2014 11:15 EDT | Provider #: 9876543<br>Smith, Ben, M.D.<br>Springfield Family Medical Associates<br>15 Main Street<br>Springfield, State ZIP |

⌐308

| Test Name | In Range | Out of Range | Reference Range |
|---|---|---|---|
| LIPID PANEL | | | |
|   TRIGLYCERIDES | | 185 h | <150 mg/dL |
|   CHOLESTEROL, TOTAL | 139 | | 125-200 mg/dL |
|   HDL CHOLESTEROL | | 30 L | > OR = 40 mg/dL |
|   LDL-CHOLESTEROL | 72 | | <130 mg/dL (calc) |
|     DESIRABLE RANGE <100 MG/DL FOR PATIENTS WITH CHD | | | |
|     OR DIABETES AND <70 MG/DL FOR DIABETIC PATIENTS | | | |
|     WITH KNOWN HEART DISEASE. | | | |
|   CHOL/HDLC RATIO | 4.5 | | < OR = 5.0 (calc) |
| BASIC METABOLIC PANEL | | | |
|   GLUCOSE | | 112 H | 65-99 mg/dL<br>FASTING REFERENCE INTERVAL |
|   UREA NITROGEN (BUN) | 23 | | 7-25 mg/dL |
|   CREATININE | 1.27 | | 0.50-1.30 mg/dL |
|   eGFR NON-AFR. AMERICAN | >60 | | > OR = 60 mL/min/1.73m2 |
|   eGFR AFRICAN AMERICAN | >60 | | > OR = 60 mL/min/1.73m2 |
|   BUN/CREATININE RATIO | N/A | | 6-22 (calc) |
|     BUN/CREATININE RATIO IS NOT REPORTED WHEN THE | | | |
|     BUN AND CREATININE VALUES ARE WITHIN NORMAL LIMITS. | | | |
|   SODIUM | 136 | | 135-146 mmol/L |
|   POTASSIUM | 5.2 | | 3.5-5.3 mmol/L |
|   CHLORIDE | 106 | | 98-110 mmol/L |
|   CARBON DIOXIDE | 21 | | 21-33 mmol/L |
|   CALCIUM | 9.5 | | 8.6-10.2 mg/dL |
| HEPATIC FUNCTION PANEL | | | |
|   PROTEIN, TOTAL | 6.6 | | 6.2-8.3 g/dL |
|   ALBUMIN | 4.1 | | 3.6-5.1 g/dL |
|   GLOBULIN | 2.5 | | 2.1-3.7 g/dL (calc) |
|   ALBUMIN/GLOBULIN RATIO | 1.6 | | 1.0-2.1 (calc) |
|   BILIRUBIN, TOTAL | 0.6 | | 0.2-1.2 gm/dL |
|   BILIRUBIN, DIRECT | 0.1 | | N OR = 0.2 mg/dL |
|   BILIRUBIN, INDIRECT | 0.5 | | 0.2-1.2 mg/dL (calc) |
|   ALKALINE PHOSPHATASE | 51 | | 40-115 U/L |
|   AST | 31 | | 10-35 U/L |
|   ALT | 31 | | 9-60 U/L |
| CBC (INCLUDES DIFF/PLT) | | | |
|   WHITE BLOOD CELL COUNT | 7.3 | | 3.8-10.8 Thousand/uL |
|   RED BLOOD CELL COUNT | 4.73 | | 4.20-5.80 Million/uL |
|   HEMOGLOBIN | 15.2 | | 13.2-17.1 g/dL |
|   HEMATOCRIT | 44.6 | | 38.5-50.0 % |
|   MCV | 92.8 | | 80.0-100.0 fL |
|   MCH | 31.6 | | 27.0-33.0 pg |
|   MCHC | 34.1 | | 32.0-36.0 g/dL |
|   RDW | 15.0 | | 11.0-15.0 % |
|   PLATELET COUNT | 154 | | 140-400 Thousand/uL |
|   MPV | 8.6 | | 7.5-11.5 fL |

FIG. 3A

| LAB COMPANY LOGO | Lab Company Name 320  316  Report Status: FINAL |
|---|---|
| | 1 Main Street |
| | Springfield, State ZIP  318  DOE, JOHN |

| Patient Information | Specimen Information | Provider Information |
|---|---|---|
| Name: John Doe | Specimen #: 12345 | Provider #: 9876543 |
| DOB: 1/1/1980 | Requisition #: 1234567 | Smith, Ben, M.D. |
| Age: 34 | | Springfield Family Medical Associates |
| Fasting: Y | Collected: 1/1/2014 10:00 EDT | |
| Gender: M | Received: 1/1/2014 15:22 EDT | 15 Main Street |
| Phone: (800) 123-4567 | Reported: 1/2/2014 11:15 EDT | Springfield, State ZIP |
| Policy ID: 5555555 | | |

| Test Name | In Range | Out of Range | Reference Range |
|---|---|---|---|
| LIPID PANEL | | | |
| TRIGLYCERIDES | | 185 h | <150 mg/dL |
| CHOLESTEROL, TOTAL | 139 | | 125-200 mg/dL |
| HDL CHOLESTEROL | | 30 L | > OR = 40 mg/dL |
| LDL-CHOLESTEROL | 72 | | <130 mg/dL (calc) |
| DESIRABLE RANGE <100 MG/DL FOR PATIENTS WITH CHD | | | |
| OR DIABETES AND <70 MG/DL FOR DIABETIC PATIENTS | | | |
| WITH KNOWN HEART DISEASE. | | | |
| CHOL/HDLC RATIO | 4.5 | | < OR = 5.0 (calc) |
| BASIC METABOLIC PANEL | | | |
| GLUCOSE | | 112 H | 65-99 mg/dL |
| | | | FASTING REFERENCE INTERVAL |
| UREA NITROGEN (BUN) | 23 | | 7-25 mg/dL |
| CREATININE | 1.27 | | 0.50-1.30 mg/dL |
| eGFR NON-AFR. AMERICAN | >60 | | > OR = 60 mL/min/1.73m2 |
| eGFR AFRICAN AMERICAN | >60 | | > OR = 60 mL/min/1.73m2 |
| BUN/CREATININE RATIO | N/A | | 6-22 (calc) |
| BUN/CREATININE RATIO IS NOT REPORTED WHEN THE | | | |
| BUN AND CREATININE VALUES AREWITHIN NORMAL LIMITS. | | | |
| SODIUM | 136 | | 135-146 mmol/L |
| POTASSIUM | 5.2 | | 3.5-5.3 mmol/L |
| CHLORIDE | 106 | | 98-110 mmol/L |
| CARBON DIOXIDE | 21 | | 21-33 mmol/L |
| CALCIUM | 9.5 | | 8.6-10.2 mg/dL |
| HEPATIC FUNCTION PANEL | | | |
| PROTEIN, TOTAL | 6.6 | | 6.2-8.3 g/dL |
| ALBUMIN | 4.1 | | 3.6-5.1 g/dL |
| GLOBULIN | 2.5 | | 2.1-3.7 g/dL (calc) |
| ALBUMIN/GLOBULIN RATIO | 1.6 | | 1.0-2.1 (calc) |
| BILIRUBIN, TOTAL | 0.6 | | 0.2-1.2 gm/dL |
| BILIRUBIN, DIRECT | 0.1 | | N OR = 0.2 mg/dL |
| BILIRUBIN, INDIRECT | 0.5 | | 0.2-1.2 mg/dL (calc) |
| ALKALINE PHOSPHATASE | 51 | | 40-115 U/L |
| AST | 31 | | 10-35 U/L |
| ALT | 31 | | 9-60 U/L |
| CBC (INCLUDES DIFF/PLT) | | | |
| WHITE BLOOD CELL COUNT | 7.3 | | 3.8-10.8 Thousand/uL |
| RED BLOOD CELL COUNT | 4.73 | | 4.20-5.80 Million/uL |
| HEMOGLOBIN | 15.2 | | 13.2-17.1 g/dL |
| HEMATOCRIT | 44.6 | | 38.5-50.0 % |
| MCV | 92.8 | | 80.0-100.0 fL |
| MCH | 31.6 | | 27.0-33.0 pg |
| MCHC | 34.1 | | 32.0-36.0 g/dL |
| RDW | 15.0 | | 11.0-15.0 % |
| PLATELET COUNT | 154 | | 140-400 Thousand/uL |
| MPV | 8.6 | | 7.5-11.5 fL |

FIG. 3C

CONCEPTS FOR EXTRACTING LAB DATA

TECHNOLOGICAL FIELD

Example embodiments of the present invention relate generally to health care and, more particularly, to methods and apparatuses that improve the computerized extraction of data from lab reports.

BACKGROUND

Applicant has discovered problems with existing computerized data extraction techniques. Through applied effort, ingenuity, and innovation, Applicant has solved many of these identified problems by developing a solution that is embodied by the present invention and described in detail below.

SUMMARY

With increasing reliance on computerized record-keeping and the increasing rigor of medical record-keeping has come a large increase in the number of lab reports, charts, and other medical documentation. While this growth in record-keeping has enabled and encouraged improvements in actuarial evaluation of medical diagnostics, procedures, and outcomes, this growth has also created problems. For instance, the explosion of complexity and number of medical records has effectively eliminated manual document processing as a practical way to ensure real-time retrieval of unstructured data and therefore prevents the timely incorporation of this data into structured relational databases that can be used for actuarial evaluation. Thus, it is increasingly important to rely upon computerized mechanisms for extracting relevant data from these documents.

However, given the complexity and number of medical records in the medical industry today traditional computerized methods of data extraction require increasingly large amounts of computing resources and suffer from similar problems as manual data extraction. In big data environments such as medical records management, even small improvements in the efficiency with which a document can be processed can produce enormous time and resource savings due to the sheer number of documents that must be processed. In turn, increases in efficiency typically produce concomitant increases in the rate of data extraction. As a result, an increase in document processing efficiency can provide more up-to-date sets of structured data for evaluation.

As alluded to above, the manipulation of big data sets is not practically possible through manual effort alone, and computationally expensive when using traditional computerized data recognition and extraction techniques. The present invention contemplates methods, apparatuses, and computer program products that improve upon existing computerized data recognition and extraction techniques by eliminating unnecessary processing steps. In this regard, some example embodiments described herein optimize the extraction of relevant data from documents such as lab reports.

In a first example embodiment, a computer-implemented method is provided for extracting lab result data from lab reports. The method includes receiving, by a computing device, a lab report, identifying, by the computing device, one or more relevant portions of the lab report, and generating, by the computing device, parsed lab report data from the identified one or more relevant portions of the lab report. The method further includes extracting, by the computing device, patient information and lab results from the parsed lab report data.

In some embodiments, the method further includes identifying, by the computing device, recognizable characteristics of the lab report, and categorizing, by the computing device, the lab report based at least in part on the recognizable characteristics of the lab report, wherein identifying the one or more relevant portions of the lab report is performed based at least in part on the categorization of the lab report. In some such embodiments, categorizing the lab report comprises identifying, based at least in part on the recognizable characteristics of the lab report, at least one of a source of the lab report or a type of the lab report. Additionally or alternatively, in some such embodiments, identifying the recognizable characteristics of the lab report utilizes a neural net. In this regard, the neural net may comprise a restricted Boltzmann machine.

In some embodiments, identifying the one or more relevant portions of the lab report includes identifying, by the computing device, one or more first portions of the lab report that contain patient information, and identifying, by the computing device, one or more second portions of the lab report that contain lab results, wherein the one or more relevant portions of the lab report include the one or more first portions and the one or more second portions. In some such embodiments, identifying the one or more first portions of the lab report identifying patient information includes retrieving, by the computing device and from a template database, one or more pixel regions associated with the one or more first portions of the lab report. Additionally or alternatively, identifying the one or more second portions of the lab report identifying lab results may comprise retrieving, by the computing device and from a template database, one or more pixel regions associated with the one or more second portions of the lab report.

In some embodiments, generating parsed lab report data from only the identified one or more relevant portions of the lab report includes parsing only the one or more relevant portions of the lab report to generate scan results corresponding to the one or more relevant portions of the lab report, and determining, based at least in part on the scan results corresponding to the one or more relevant portions of the lab report, structured word sequences corresponding to the one or more relevant portions of the lab report, wherein the parsed lab report data comprises the structured word sequences.

In another example embodiment, an apparatus is provided for extracting lab result data from lab reports. The apparatus includes at least one processor and at least one memory including program code, the at least one memory and the program code configured to, with the processor, cause the apparatus to at least receive a lab report, identify one or more relevant portions of the lab report, and generate parsed lab report data from the identified one or more relevant portions of the lab report. The at least one memory and the program code are further configured to, with the processor, cause the apparatus to extract patient information and lab results from the parsed lab report data.

In some embodiments, the at least one memory and the program code are further configured to, with the processor, cause the apparatus to identify recognizable characteristics of the lab report, and categorize the lab report based at least in part on the recognizable characteristics of the lab report, wherein the at least one memory and the program code are further configured to, with the processor, cause the apparatus to identify the one or more relevant portions of the lab report based at least in part on the categorization of the lab report. In some such embodiments, categorizing the lab report includes identifying, based at least in part on the recognizable characteristics of the lab report, at least one of a source of the lab report or a type of the lab report. Additionally or alternatively, in some such embodiments, the at least one memory and the program code are further configured to, with the processor, cause the apparatus to identify the recognizable characteristics of the lab report utilizing a neural net. In this regard, the neural net may comprise a restricted Boltzmann machine.

In some embodiments, identifying the one or more relevant portions of the lab report includes identifying one or more first portions of the lab report that contain patient information, and identifying one or more second portions of the lab report that contain lab results, wherein the one or more relevant portions of the lab report include the one or more first portions and the one or more second portions. In some such embodiments, identifying the one or more first portions of the lab report identifying patient information includes retrieving, from a template database, one or more pixel regions associated with the one or more first portions of the lab report. Additionally or alternatively, identifying the one or more second portions of the lab report identifying lab results may comprise retrieving, from a template database, one or more pixel regions associated with the one or more second portions of the lab report.

In some embodiments, generating parsed lab report data from only the identified one or more relevant portions of the lab report includes parsing only the one or more relevant portions of the lab report to generate scan results corresponding to the one or more relevant portions of the lab report, and determining, based at least in part on the scan results corresponding to the one or more relevant portions of the lab report, structured word sequences corresponding to the one or more relevant portions of the lab report, wherein the parsed lab report data comprises the structured word sequences.

In yet another example embodiment, a non-transitory computer-readable storage medium is provided for extracting lab result data from lab reports. The non-transitory computer-readable storage medium storing program code instructions that, when executed, cause a computing device to receive a lab report, identify one or more relevant portions of the lab report, and generate parsed lab report data from the identified one or more relevant portions of the lab report. The program code instructions, when executed, further cause the computing device to extract patient information and lab results from the parsed lab report data.

In some embodiments, the program code instructions, when executed, further cause the computing device to identify recognizable characteristics of the lab report, and categorize the lab report based at least in part on the recognizable characteristics of the lab report, wherein the program code instructions, when executed, further cause the computing device to identify the one or more relevant portions of the lab report based at least in part on the categorization of the lab report. In some such embodiments, categorizing the lab report includes identifying, based at least in part on the recognizable characteristics of the lab report, at least one of a source of the lab report or a type of the lab report. Additionally or alternatively, in some such embodiments, the program code instructions, when executed, further cause the computing device to identify the recognizable characteristics of the lab report utilizing a neural net. In this regard, the neural net may comprise a restricted Boltzmann machine.

In some embodiments, identifying the one or more relevant portions of the lab report includes identifying one or more first portions of the lab report that contain patient information, and identifying one or more second portions of the lab report that contain lab results, wherein the one or more relevant portions of the lab report include the one or more first portions and the one or more second portions. In some such embodiments, identifying the one or more first portions of the lab report identifying patient information includes retrieving, from a template database, one or more pixel regions associated with the one or more first portions of the lab report. Additionally or alternatively, identifying the one or more second portions of the lab report identifying lab results may comprise retrieving, from a template database, one or more pixel regions associated with the one or more second portions of the lab report.

In some embodiments, generating parsed lab report data from only the identified one or more relevant portions of the lab report includes parsing only the one or more relevant portions of the lab report to generate scan results corresponding to the one or more relevant portions of the lab report, and determining, based at least in part on the scan results corresponding to the one or more relevant portions of the lab report, structured word sequences corresponding to the one or more relevant portions of the lab report, wherein the parsed lab report data comprises the structured word sequences.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
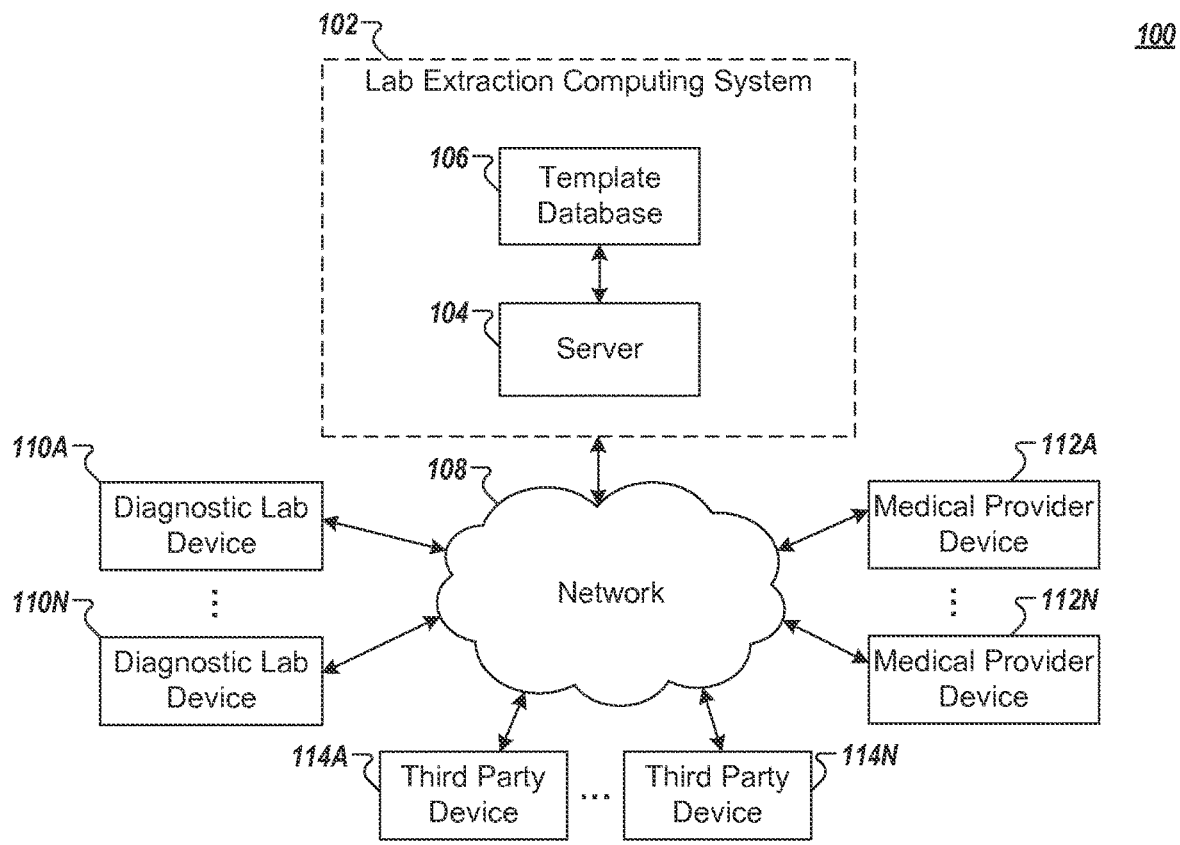
Figure 2:
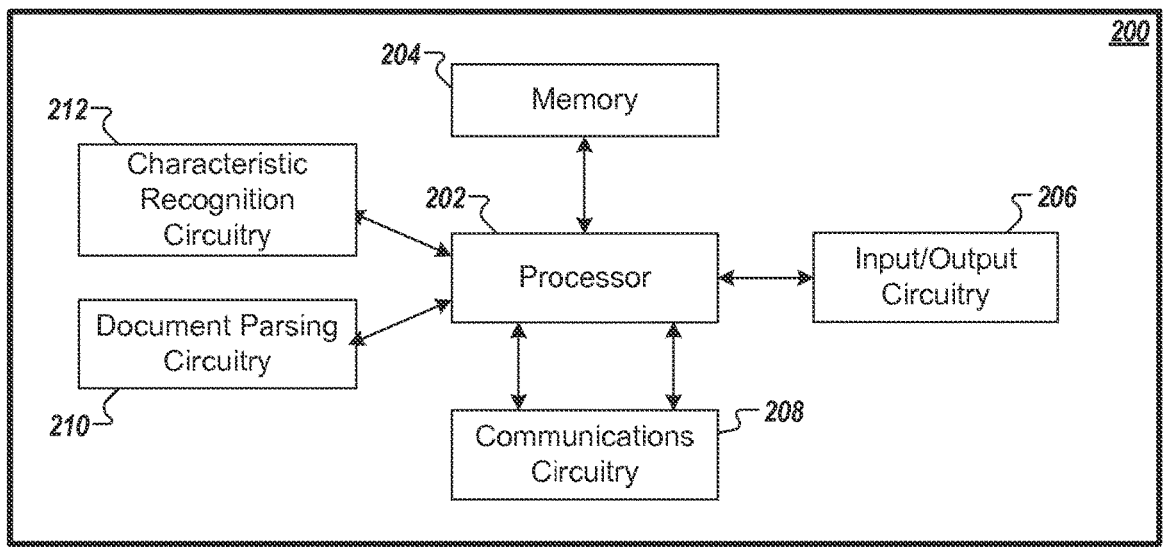
Figure 3B:
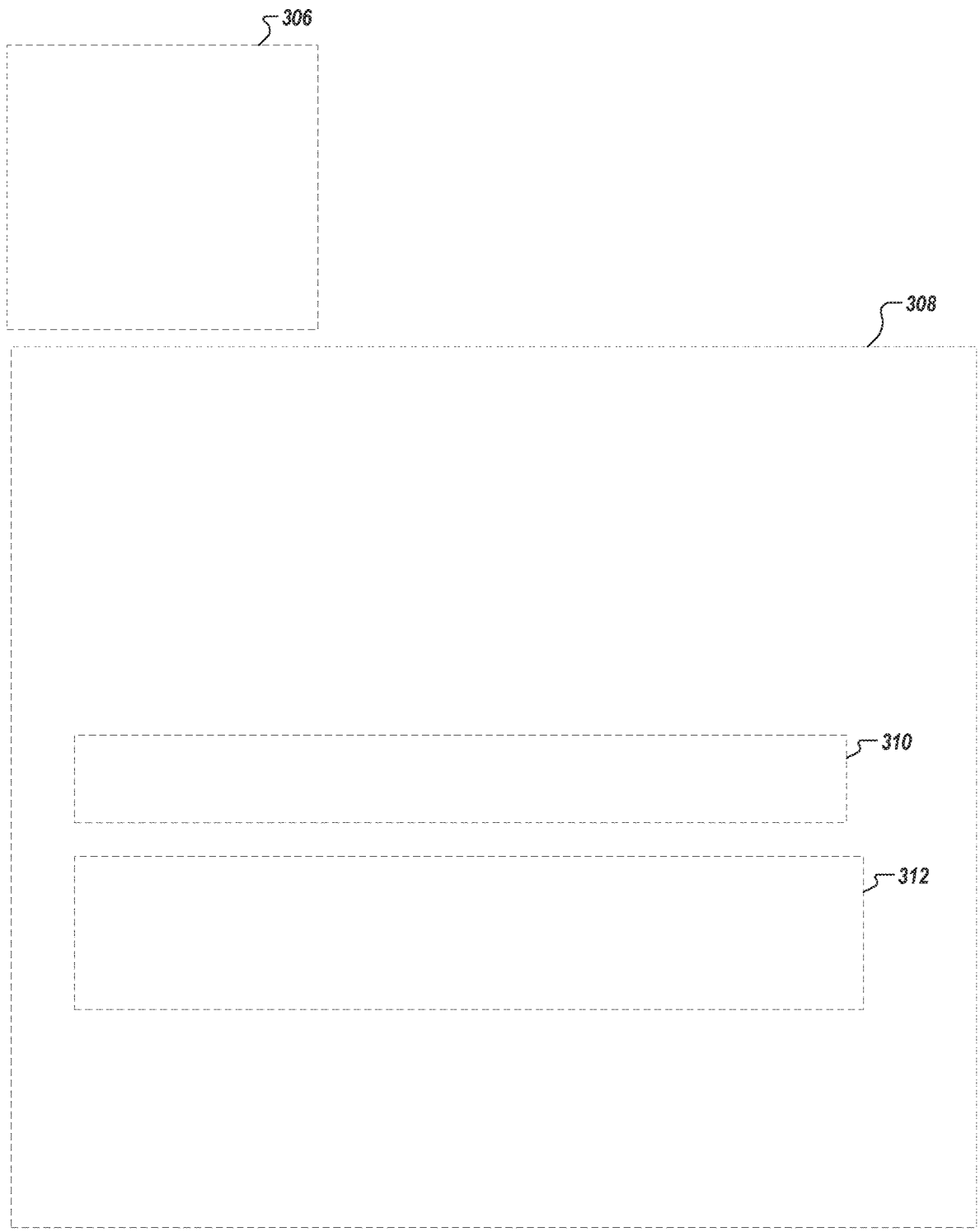
Figure 4:
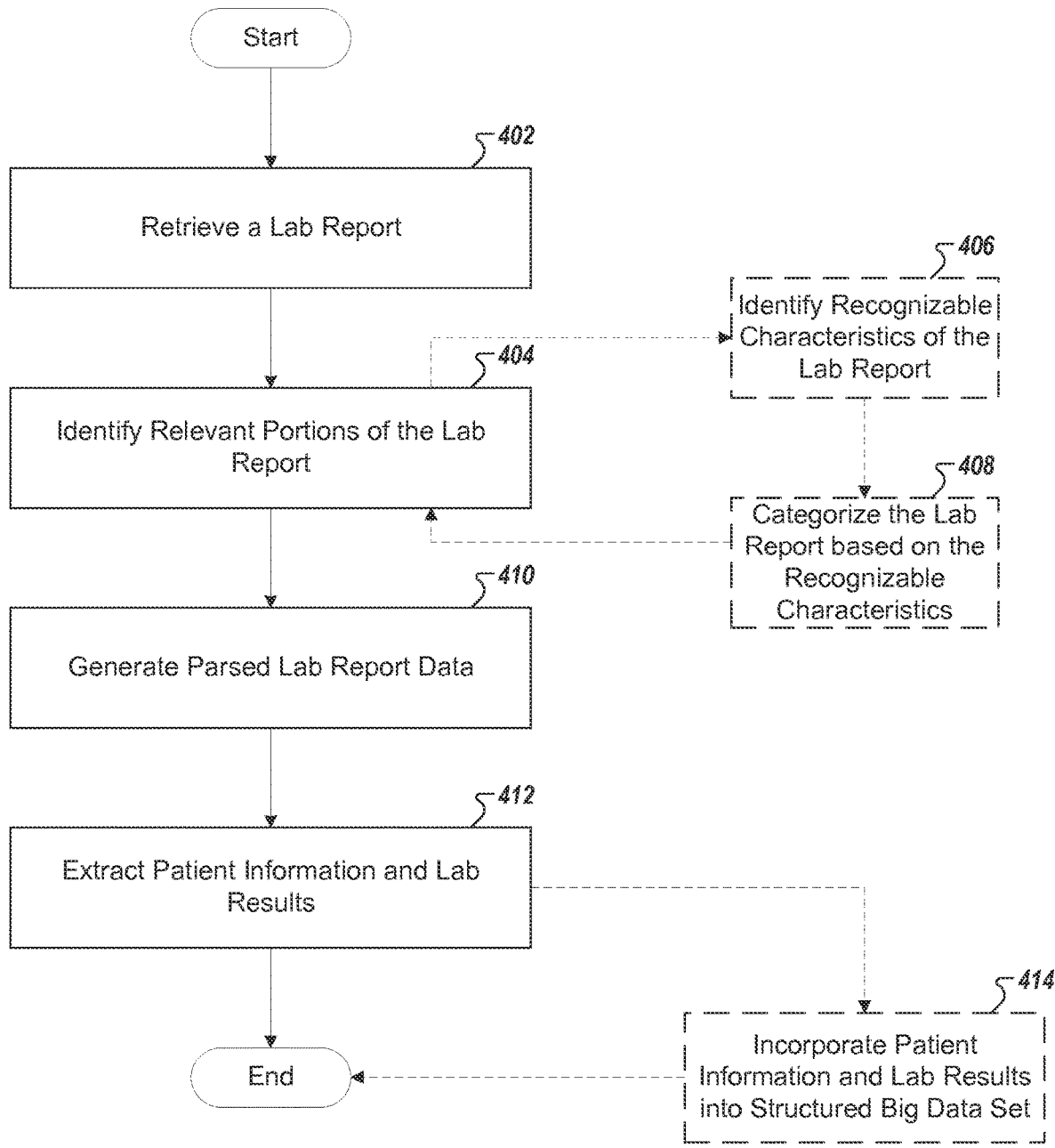
Figure 5:
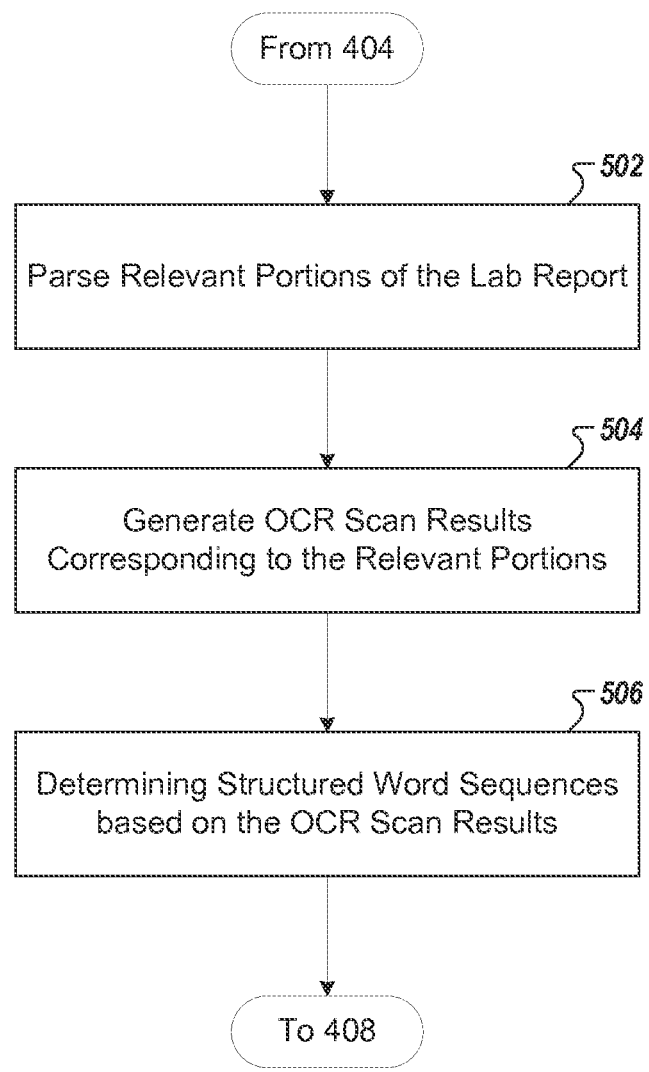

Having thus described certain example embodiments of the present disclosure in general terms, reference will now be made to the accompanying drawings, which are not necessarily drawn to scale, and wherein:

FIG. 1 shows an example system diagram, in accordance with an example embodiment of the present invention;

FIG. 2 illustrates a schematic block diagram of circuitry used in association with a lab extraction computing device, in accordance with some example embodiments;

FIG. 3A illustrates an example lab report, in accordance with some example embodiments;

FIG. 3B illustrates relevant portions of the example lab report of FIG. 3A, in accordance with some example embodiments;

FIG. 3C illustrates non-relevant portions of the example lab report of FIG. 3A, in accordance with some example embodiments;

FIG. 4 illustrates a flowchart describing example operations for extracting patient information and lab results, in accordance with some example embodiments; and FIG. 5 illustrates a flowchart describing example operations for generating parsed lab report data, in accordance with some example embodiments.

DETAILED DESCRIPTION

Various embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

As used herein, the term "lab reports" refers to various records and documentation that may exist in a number of different formats. For instance, a lab report may have originally been a paper record that were scanned and stored in a database as an image file. As another example, a lab report may be a portable document format (PDF) documents created by a computer. Of course, lab reports may be stored in any other file format as well. In any event, lab reports may comprise any number of different documents that may be received from a medical service provider (e.g., a doctor or doctor's office), a diagnostic laboratory, a health insurer, a patient, or any other party that may generate or have access to a patient's medical information. It will be understood that references to "lab reports" below should not be viewed as limiting the scope or nature of the documentation that may be analyzed using techniques described herein. Rather, the analysis of lab reports is provided for ease of understanding only, and example embodiments may analyze any type of computerized documentation without departing from the spirit or scope of the present invention.

Technical Foundations

As noted previously, the increasing reliance on computerized record-keeping and the increasing rigor of medical record-keeping has introduced a large increase in the number of lab reports accessible by those in the medical field. While this growth in record-keeping has enabled and encouraged improvements in actuarial evaluation of medical diagnostics, procedures, and outcomes, this growth has eliminated manual document processing as a practical way to ensure accurate or near real-time retrieval of unstructured data, and therefore prevents the timely incorporation of this data into structured databases that can be used for evaluation. Thus, it is increasingly important to rely upon computerized mechanisms for extracting relevant data from these documents.

However, given the complexity and number of medical records in the medical industry today traditional computerized methods of data extraction require increasingly large amounts of computing resources and suffer from similar problems as manual data extraction. In big data environments such as medical records management, even small improvements in the efficiency with which a document can be processed can produce enormous time and resource savings due to the sheer number of documents that must be processed. In turn, increases in efficiency typically produce concomitant increases in the rate of data extraction. As a result, an increase in document processing efficiency can provide more up-to-date sets of structured data for evaluation.

Various embodiments described herein improve upon existing computerized data recognition and extraction techniques by eliminating unnecessary processing steps. To be clear, the embodiments described herein are directed to improvements in the technical character, ability, and efficiency of the computerized data extraction performed by computing devices.

System Architecture and Example Apparatus

Methods, apparatuses, and computer program products of the present invention may be embodied by any of a variety of devices. For example, the method, apparatus, and computer program product of an example embodiment may be embodied by a networked device, such as a server or other network entity, configured to communicate with one or more devices, such as one or more client devices. Additionally or alternatively, the computing device may include fixed computing devices, such as a personal computer or a computer workstation. Still further, example embodiments may be embodied by any of a variety of mobile terminals, such as a portable digital assistant (PDA), mobile telephone, smartphone, laptop computer, tablet computer, or any combination of the aforementioned devices.

In this regard, FIG. 1 discloses an example computing system within which embodiments of the present invention may operate. Diagnostic laboratories, medical providers, and other third parties may access and upload lab reports to a lab extraction computing system 102 via a network 108 (e.g., the Internet, or the like) using computing devices 110A through 110N, 112A through 112N, and 114A through 114N, respectively.

The computing devices 110A through 110N, 112A through 112N, and 114A through 114N may be embodied by any computing devices known in the art. Electronic data received by the server 104 from the diagnostic laboratory devices 110A-110N, medical provider devices 112A-112N, and third party devices 114A-114N may be provided in various forms and via various methods. For example, these devices may include desktop computers, laptop computers, smartphones, netbooks, tablet computers, wearable devices, and/or any combination of devices or entities adapted to perform the functions, operations, and/or processes described herein, and the electronic data may be provided using various transmission modes and/or protocols associated with these devices.

Additionally or alternatively, the diagnostic laboratories, medical providers, and other third parties may interact with the lab extraction computing system 102 via a web browser. As yet another example, the devices 110A-110N, 112A-112N, and 114A-114N may include various hardware or firmware designed to interface with the lab extraction computing system 102 (e.g., where an example device 110, 112, or 114 is a purpose-built device offered for the primary purpose of communicating with the lab extraction computing system service 102, such as a kiosk).

The lab extraction computing system 102 may comprise a server 104 in communication with a template database 106. The server 104 may be embodied as a computer or computers as known in the art. The server 104 may receive electronic data from various sources, including but not necessarily limited to the devices 110A-110N, 112A-112N, and 114A-114N and may be operable to receive and process lab reports provided by these devices.

The template database 106 may be embodied as a data storage device such as a Network Attached Storage (NAS) device or devices, or as a separate database server or servers. The template database 106 includes information accessed and stored by the server 104 to facilitate the operations of the lab extraction computing system 102. For example, the template database 106 may include, without limitation: user account credentials for system administrators, diagnostic laboratories, medical providers, and third parties; and sets of structured data (e.g., relational databases) correlating patient information with test results, procedures, and outcomes that are known a priori or determined via processing of lab reports by the lab extraction computing system 102, and/or the like. As may be most relevant to embodiments described herein, template database 106 may include lab report templates that contain information regarding relevant portions of lab reports having particular defining characteristics.

In this regard, a lab report template may illustrate patient information within particular known pixel regions and may disclose lab results within other particular known pixel regions. For instance, a first laboratory may prepare all of its lab reports in a particular way so that patient information is always located in a first region and results are always located in another region. A lab report templates may thus be used for all lab reports from the first laboratory. Alternatively, it may be the case that, for some types of lab reports, every laboratory prepares lab reports displaying data in a uniform arrangement (e.g., when a uniform display is demanded by law or regulation). For instance, blood panel lab reports may have similar arrangements of text and white space. For such situations, a single lab report template may be used for all lab reports of these types, irrespective of the source of the lab reports.

In any event, template database 106 may store lab report templates that identify the pixel regions in which different types of data may be retrieved from similar lab reports. In this regard, each lab report template may store this information as a node in a tree that describes the document structure associated with the lab reports within the lab report template. This node may include a set of coordinates that could describe a polygon that could be expressed in XML or JSON. In turn, the lab report template may then be stored within template database 106.

Example Apparatus for Implementing Embodiments of the Present Invention

The server 104 may be embodied by one or more computing devices, such as apparatus 200 shown in FIG. 2. As illustrated in FIG. 2, the apparatus 200 may include a processor 202, a memory 204, input/output circuitry 206, communications circuitry 208, document parsing circuitry 210, and characteristic recognition circuitry 212. The apparatus 200 may be configured to execute the operations described above with respect to FIG. 1 and below with respect to FIGS. 4 and 5. Although these components 202-212 are described with respect to functional limitations, it should be understood that the particular implementations necessarily include the use of particular hardware. It should also be understood that certain of these components 202-212 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus therefore includes particular hardware configured to perform the functions associated with the particular circuitry described herein.

Of course, while the term "circuitry" should be understood broadly to include hardware, in some embodiments it may also include software for configuring the hardware. In some embodiments, "circuitry" may include processing circuitry, storage media, network interfaces, input/output devices, and the like. In some embodiments, other elements of the apparatus 200 may provide or supplement the functionality of particular circuitry. For example, the processor 202 may provide processing functionality, the memory 204 may provide storage functionality, the communications circuitry 208 may provide network interface functionality, and the like.

The processor 202 (and/or co-processor or any other processing circuitry assisting or otherwise associated with the processor) may be in communication with the memory 204 via a bus for passing information among components of the apparatus. The memory 204 may be non-transitory and may include, for example, one or more volatile and/or non-volatile memories. In other words, the memory may be an electronic storage device (e.g., a computer readable storage medium). The memory 204 may be configured to store information, data, content, applications, instructions, or the like, for enabling the apparatus to carry out various functions in accordance with example embodiments of the present invention.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 202 may be configured to execute instructions stored in the memory 204 or otherwise accessible to the processor. Alternatively or additionally, the processor may be configured to execute hard-coded functionality. As such, whether configured by hardware or software methods, or by a combination of hardware with software, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the apparatus 200 may include input/output circuitry 206 that may, in turn, be in communication with processor 202 to provide output to a user and, in some embodiments, to receive an indication of user input. The input/output circuitry 206 may comprise a user interface and may include a display and may comprise a web user interface, a mobile application, a client device, a kiosk, or the like. In some embodiments, the input/output circuitry 206 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the apparatus 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

Document parsing circuitry 210 includes hardware configured to perform optical character recognition (OCR) and word sequence analysis of a given document. To this end, document parsing circuitry 210 may operate in any number of ways as may be understood in the art. One such example document parsing concept is described in U.S. patent application Ser. No. 14/336,416, titled "TARGETED OPTICAL CHARACTER RECOGNITION (OCR) FOR MEDICAL TERMINOLOGY" and filed on Jul. 21, 2014, the entire contents of which are incorporated herein by reference. It should be understood that other methods of OCR analysis and word identification are contemplated herein. The document parsing circuitry 210 is capable of parsing, using an OCR technique, only the one or more relevant portions of the lab report to generate scan results corresponding to the one or more relevant portions of the lab report. The document parsing circuitry 210 is further configured to determine, based on the scan results corresponding to the one or more relevant portions of the lab report, structured word sequences corresponding to the one or more relevant portions of the lab report. The document parsing circuitry 210 may then output the structured word sequences as parsed lab report data.

It should be understood that while document parsing circuitry 210 might be configured to utilize OCR techniques to generate scan results, in some embodiments the document parsing circuitry 210 may instead utilize optical word recognition, and recognize text on a word-by-word level, rather than on a character-by-character level. Furthermore, because a portion of a lab report may have very few possible configurations, in some embodiments the document parsing circuitry 210 can associate the raw image of that portion of the lab report, as a whole, with a particular set of information. For instance, some lab reports might merely indicate a positive or negative result, in which case parsing of the results portion of that type of lab report on a character-by-character or word-by-word level may be unnecessary and inefficient, and the raw image of the portion can directly be recognized as either a positive result or a negative result.

Moreover, it should be understood that the document parsing circuitry 210 may additionally or alternatively utilize any other computer vision techniques to harvest information from lab reports. For instance, a Hierarchical Hidden Markov Model may be used to classify the content of a portion of a lab report based on probabilities of occurrence of various information inside the portion of the lab report.

Document parsing circuitry 210 may utilize processing circuitry, such as the processor 202, to perform the above operations, and may utilize memory 204 to store the generated scan results and/or parsed lab report data. It should also be appreciated that, in some embodiments, the document parsing circuitry 210 may include a separate processor, specially configured field programmable gate array (FPGA), or application specific interface circuit (ASIC) to perform optical character recognition or structured word sequence generation. The document parsing circuitry 210 is therefore implemented using hardware components of the apparatus which in turn are configured by either hardware or software for implementing these planned functions.

Characteristic recognition circuitry 212, in contrast, may often operate before application of document parsing circuitry 210. To this end, characteristic recognition circuitry 212 may evaluate lab reports upon initial receipt thereof to identify recognizable characteristics that may enable efficiency gains in the data extraction process. These recognizable characteristics may comprise source-identifying logos and/or words (e.g., the contents of boxes 302 and 304, as shown in FIG. 3A). Similarly, these recognizable characteristics may comprise particular arrangements of text and white space throughout a lab report (which may, for example, be indicative of particular types of test results that would indicate a type of the lab report under evaluation). By identifying these types of recognizable characteristic of the lab report, characteristic recognition circuitry 212 can categorize the lab report based on the source of the lab report or the type of information contained in the lab report. As a result of this categorization, characteristic recognition circuitry 212 can query lab report template database 106 to identify one or more lab report templates that may indicate the relevant portions of a given lab report.

To produce these results, characteristic recognition circuitry 212 may utilize a neural net that trains, over time, to become more adept at identifying characteristics and categorizing lab reports. More particularly, the neural net may be a restricted Boltzmann machine (RBM). To this end, an RBM can be used as a general classifier to recognize a shape or image as well as any structure or pattern. Thus, as utilized in some embodiments, the RBM is trained to recognize characteristics of received lab reports that indicate categories into which the lab reports should be classified, and thus to select the correct lab report template to utilize for extracting information from the lab reports.

Characteristic recognition circuitry 210 may utilize processing circuitry, such as the processor 202, to perform the above operations, and may utilize memory 204 to store information regarding the categorization of lab reports. It should also be appreciated that, in some embodiments, the characteristic recognition circuitry 212 may include a separate processor, specially configured field programmable gate array (FPGA), or application specific interface circuit (ASIC) to perform characteristic recognition. The characteristic recognition circuitry 212 is therefore implemented using hardware components of the apparatus which in turn are configured by either hardware or software for implementing these planned functions.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example displays discussed herein can be based on data that is received, generated and/or maintained by one or more components of apparatus 200. In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Operations Performed by the Lab Extractor

Having described the circuitry comprising embodiments of the present invention, it should be understood that the lab extraction computing system 102 may advantageously extract patient and lab result data in a number of ways. In accordance with example embodiments, FIGS. 3A through 3C illustrate a high-level overview of one mechanism by which embodiments disclosed herein operating with increased efficiency, while FIGS. 4 and 5 illustrate flowcharts containing specific operations performed to efficiently and extract patient information and lab result data.

Turning now to FIG. 3A, an example lab report is illustrated. It should be understood that while this example lab report provides a particular layout of patient information and lab results, other lab reports will provide different layouts of this data based primarily on the diagnostic laboratory source of the lab report and the type of the lab report (e.g., if it reports the results of laboratory tests, the particular tests performed may influence the presentation of the lab results; if the lab report is, in fact, a medical chart or other type of document, then this categorization of the lab report will also influence the nature and location of patient and lab result information). However, for illustrative purposes, the example lab report of FIG. 3A demonstrates a particular standardized presentation of patient and lab result information.

Box 302 illustrates a source-identifying element of this lab report (and, indeed, many medical documents have source-identifying logos or text located in the upper left hand corner of the documentation, although it should be appreciated that source-identifying logos or text may be present in a number of different locations in a document). Characteristic recognition circuitry 212 may utilize the information in box 302 to categorize the lab report. Moreover, characteristic recognition circuitry 212 may further be trained, over time, to identify the existence of significant characteristic information (and thus may improve at identifying and categorizing source-identifying elements, such as box 302, as more and more lab reports are analyzed. In this regard, the information contained in box 304 may comprise more specific source-identifying information that may be utilized by characteristic recognition circuitry 212. In some embodiments, the source of the lab report may be known because of where it was retrieved from (e.g., if the lab report was deposited by a diagnostic lab device 110, it may be inferred that the source of the lab report is the respective diagnostic laboratory), but in the more general scenarios, information about where a lab report was retrieved from provides another data point, in addition to the information from box 302, box 304, and/or any other source-identifying region, that could be used to recognize example characteristics of a lab report.

Upon categorization of the example lab report, the lab extraction computing system 102 may retrieve information (e.g., a lab report template) from template database 106 indicating the portions of the lab report that provide patient information and/or lab result information. These relevant portions may, in some embodiments, be identified using pixel regions of the lab report. Using this information, the lab extraction computing system 102 can identify that the box 306 contains patient information, while the information contained in box 308 represents tests run and lab results. In some embodiments, more granular pixel regions may be retrieved from template database 106 indicating areas corresponding to lab results for particular tests. For instance, box 310 identified in this example illustrates lab results regarding electrolytes, while box 312 illustrates lab results regarding liver function.

Additionally or alternatively, the lab extraction computing system 102 may perform clustering based on the whitespace on the page to identify clear boundaries that are likely to signify breaks between distinct types of information. Such embodiments essentially employ a heuristic that it is unlikely for there to be whitespace within a contiguous section of a lab report. Such clustering may be performed in a recursive manner, to identify all permutations that might fit a predefined format.

While FIG. 3A overlays relevant portions of an example lab report for the sake of explanation, FIG. 3B illustrates a more accurate understanding of how the pixel regions identified by boxes 306, 308, 310, and 312 might be stored (e.g., as a lab report template) by template database 106, because FIG. 3B strips out any information regarding a specific document, leaving only an identification of relevant regions associated with a particular document type. In FIG. 3B, a specific example of a lab report is not needed for the template database 106 to store information reflecting where, on any given lab report in a particular category, relevant patient information and lab results would be located. Utilizing this information, example embodiments described herein are able to improve efficiency by only parsing those portions of the lab report that correspond to one of the highlighted pixel regions.

FIG. 3C illustrates the same example lab report shown in FIG. 3A. However, in contrast to FIG. 3A, FIG. 3C highlights portions of this example lab report that can advantageously be ignored to increase data extraction efficiency and reduce the processing burden on the lab extraction computing system 102 caused by parsing this example lab report. The text shown in box 316, which illustrates headline information regarding the lab report in question, illustrates an area of the lab report that may not be necessary to parse and/or examine at all. In particular, although the patient name is listed in this area of the lab report, because sufficient identifying information is found elsewhere in the report, recognition of the patient name within box 316 would comprise duplicative effort. The other text within box 316 illustrates the status of the lab report itself (e.g., whether it is finalized or not), which can be safely ignored in this example embodiment, due to the fact that, because the lab extraction computing system 102 possesses the lab report, it is likely that the report has been finalized.

Similarly, the text shown in box 318, which illustrates specimen information and provider information, is irrelevant to the patient information and lab results that can be scraped from other portions of the report. Accordingly, the portion of this example lab report shown in box 318 can also be safely ignored to produce efficiency gains in the analysis of the lab report.

Finally, the portion of the lab report within box 320 may or may not be important information. As discussed below, categorization of the lab report, which leads to an identification of the relevant portions of the lab report, may be performed on the basis of the source of the lab report. Accordingly, the data in box 320 may be a useful source identifier of the lab report. However, even in this case, this portion of the lab report may not be relevant once the lab report has already been categorized, because the information in box 320 does not include patient information or lab result information.

Turning now to FIG. 4, the provided flowchart illustrates a sequence of operations for extracting patient information and lab results. As noted previously, these operations may be performed by a lab extraction computing system 102, with the assistance of, and/or under the control of a computing device such as apparatus 200.

In operation 402, apparatus 200 includes means, such as communications circuitry 208 or the like, for receiving a lab report. While in some embodiments, the lab report may be an unknown type of document and may be received without any source-identifying information, in other embodiments, some source identifying information may be known simply by the type and/or location of the device transmitting the lab report (e.g., if a diagnostic lab device 110 transmits the data, then there is a high probability that the diagnostic laboratory is the source of the lab report). In this regard, a single laboratory may transmit an index of patient information alongside documents including images of corresponding lab reports. In such situations, source-identifying contextual information will thus be known about each of the lab report images.

In operation 404, apparatus 200 includes means, such as characteristic recognition circuitry 212 or the like, for identifying, by a processor of the computing device, one or more relevant portions of the lab report. When some source or type identifying information is known a priori, relevant portions of the lab report can be identified based on a simple comparison to relevant information (e.g., lab reports associated with particular lab report templates, or lab report templates themselves) stored in template database 106. However, in circumstances where no source or type information is initially known, the procedure may continue to operations 406 and 408.

In operation 406, the apparatus 200 may include means, such as characteristic recognition circuitry 212 or the like, for identifying recognizable characteristics of the lab report. As noted previously, these recognizable characteristics may comprise source-identifying logos and/or words (e.g., the contents of boxes 302 and 304 shown in FIG. 3A). Alternatively, these recognizable characteristics may comprise particular arrangements of text and white space throughout a lab report (which may, for example, be indicative of particular types of test results that would indicate a type of the lab report under evaluation). To perform this identification, the characteristic recognition circuitry 212 may include a neural net that iteratively identifies new correlations between characteristics of lab reports and over time improves upon its ability to predictively model the meaning of the characteristics identified in any given target lab report. To this end, some embodiments of the present invention may utilize a restricted Boltzmann machine to perform this machine learning functionality.

In operation 408, the apparatus 200 may include means, such as characteristic recognition circuitry 212 or the like, for categorizing the lab report based on the recognizable characteristics of the lab report. To this end, categorizing the lab report can include identifying, based on the recognizable characteristics of the lab report, at least one of a source of the lab report or a type of the lab report.

Following categorization of the lab report, the apparatus 200 may return to operation 404 for identification of one or more relevant portions of the lab report. In some embodiments, identifying the one or more relevant portions of the lab report includes two disparate steps: identifying one or more first portions of the lab report that contain patient information, and identifying one or more second portions of the lab report that contain lab results. The one or more first portions of the lab report containing patient information may be identified using pixel regions corresponding to the one or more first portions of the lab report. Similarly, the one or more second portions of the lab report identifying lab results may include one or more pixel regions corresponding to the one or more second portions of the lab report.

Subsequently, in operation 410, apparatus 200 includes means, such as document parsing circuitry 210 or the like, for generating parsed lab report data from only the identified one or more relevant portions of the lab report. The operations involved in generating parsed lab report data are described in greater detail below in conjunction with FIG. 5. In operation 412, apparatus 200 includes means, such as processor 202 or the like, for extracting patient information and lab results from the parsed lab report data.

Finally, in operation 414, the apparatus 200 may include means, such as processor 202 or the like, for incorporating the patient information and lab results into a structured data set. When performed by a healthcare company, this data can subsequently be used for evaluation of patient information, diagnostics, procedures, and outcomes, and even for predictive modeling of future patient health concerns.

Turning now to the FIG. 5, a series of operations are illustrated for generating parsed lab report data. As with FIG. 4, these operations may be performed by a lab extraction computing system 102, with the assistance of, and/or under the control of a computing device such as apparatus 200.

In operation 502, the apparatus 200 may include means, such as document parsing circuitry 210 or the like, for parsing, using an optical character recognition (OCR) technique, only the one or more relevant portions of the lab report. As described above, in some embodiments this parsing may comprise character-by-character text identification, word-by-word text identification, or raw image identification, or any other type of glyph recognition operation.

In operation 504, the apparatus 200 may include means, such as document parsing circuitry 210 or the like, for generating scan results corresponding to the one or more relevant portions of the lab report.

Finally, in operation 506, the apparatus 200 may include means, such as document parsing circuitry 210 or the like, for determining, based on the scan results corresponding to the one or more relevant portions of the lab report, structured word sequences corresponding to the one or more relevant portions of the lab report.

FIGS. 4 and 5 illustrate flowcharts of the operation of an apparatus, method, and computer program product according to example embodiments of the invention. It will be understood that each block of the flowcharts, and combinations of blocks in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory of an apparatus employing an embodiment of the present invention and executed by a processor of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

Accordingly, blocks of the flowcharts support combinations of means for performing the specified functions and combinations of operations for performing the specified functions. It will be understood that one or more blocks of the flowcharts, and combinations of blocks in the flowcharts, can be implemented by special purpose hardware-based computer systems which preform the specified functions, or combinations of special purpose hardware and computer instructions.

In some embodiments, certain ones of the operations above may be modified or further amplified. Furthermore, in some embodiments, additional optional operations may be included. Modifications, amplifications, or additions to the operations above may be performed in any order and in any combination.

As described above, certain example embodiments of the present invention are directed to improved apparatuses, methods, and computer readable media for improving upon the technical character, ability, and efficiency of traditional computing devices. Through the use of data-based heuristics referenced above, embodiments described herein enable data extraction operations to ignore portions of lab reports containing irrelevant information. In this fashion, embodiments described herein provide improvements in efficiency that increase in the throughput of data extraction efforts, and enable the generation of more up-to-date sets of structured data for subsequent actuarial uses (among others).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A computer-implemented method for extracting patient data and lab result data from parsed lab report data, the method comprising:
   receiving, by a computing device, an electronic file, wherein (a) the electronic file (i) comprises a lab report and (ii) identifies a two-dimensional array of pixels, and (b) the lab report is categorized as an unknown type of lab report;
   automatically identifying, by the computing device, one or more recognizable characteristics of the lab report, wherein the one or more recognizable characteristics are selected from the group consisting of a logo, text, white space, and an arrangement of text;
   automatically categorizing, by the computing device and based at least in part on the identified one or more recognizable characteristics, the lab report as a known type of lab report;
   responsive to automatically categorizing the lab report as the known type of lab report, retrieving, by the computing device from a template database, a template corresponding to the known type of lab report, wherein the template identifies (a) a first set of one or more pixel regions in the two-dimensional array of pixels, the first set of one or more pixel regions associated with a first set of one or more relevant portions of the lab report comprising patient data, and (b) a second set of one or more pixel regions in the two-dimensional array of pixels, the second set of one or more pixel regions associated with a second set of one or more relevant portions of the lab report comprising lab result data; and
   after retrieving the template:
      identifying, by the computing device and based at least in part on the template, the first set of one or more pixel regions and the second set of one or more pixel regions, wherein (a) the first set of one or more pixel regions comprises the patient data and (b) the second set of one or more pixel regions comprises the lab result data,
      parsing, by the computing device and based at least in part on the template, (a) only the first set of one or more pixel regions and (b) only the second the second set of one or more pixel regions, to generate parsed lab report data from the identified first set of one or more pixel regions and the identified second set of one or more pixel regions by applying one or more optical character recognition techniques, and extracting, by the computing device, the patient data and the lab result data from the parsed lab report data.

2. The computer-implemented method of claim 1, wherein automatically categorizing the lab report comprises identifying at least one of a source of the lab report.

3. The computer-implemented method of claim 1, wherein identifying the recognizable characteristics of the lab report utilizes a neural net.

4. The computer-implemented method of claim 3, wherein the neural net comprises a restricted Boltzmann machine.

5. The computer-implemented method of claim 1, wherein generating parsed lab report data comprises:

determining, based at least in part on the scan results corresponding to the first set of one or more relevant portions of the lab report, structured word sequences corresponding to the one or more relevant portions of the lab report, wherein the parsed lab report data comprises the structured word sequences.

6. An apparatus for extracting patient data and lab result data from parsed lab report data, the apparatus comprising at least one processor and at least one memory including program code, the at least one memory and the program code configured to, with the processor, cause the apparatus to at least:

receive an electronic file, wherein (a) the electronic file (i) comprises a lab report and (ii) identifies a two-dimensional array of pixels, and (b) the lab report is categorized as an unknown type of lab report;

automatically identify one or more recognizable characteristics of the lab report, wherein the one or more recognizable characteristics are selected from the group consisting of a logo, text, white space, and an arrangement of text;

automatically categorize, based at least in part on the identified one or more recognizable characteristics, the lab report as a known type of lab report;

responsive to automatically categorizing the lab report as the known type of lab report, retrieve, from a template database, a template corresponding to the known type of lab report, wherein the template identifies (a) a first set of one or more pixel regions in the two-dimensional array of pixels, the first set of one or more pixel regions associated with a first set of one or more relevant portions of the lab report comprising patient data, and (b) a second set of one or more pixel regions in the two-dimensional array of pixels, the second set of one or more pixel regions associated with a second set of one or more relevant portions of the lab report comprising lab result data; and after retrieving the template:

identify, based at least in part on the template, the first set of one or more pixel regions and the second set of one or more pixel regions, wherein (a) the first set of one or more pixel regions comprises the patient data and (b) the second set of one or more pixel regions comprises the lab result data, parse, based at least in part on the template, (a) only the first set of one or more pixel regions and (b) only the second the second set of one or more pixel regions to generate parsed lab report data from the identified first set of one or more pixel regions and the identified second set of one or more pixel regions by applying one or more optical character recognition techniques, and extract the patient data and the lab result data from the parsed lab report data.

7. The apparatus of claim 6, wherein automatically categorizing the lab report comprises identifying at least one of a source of the lab report.

8. The apparatus of claim 6, wherein the at least one memory and the program code are further configured to, with the processor, cause the apparatus to identify the recognizable characteristics of the lab report utilizing a neural net.

9. The apparatus of claim 8, wherein the neural net comprises a restricted Boltzmann machine.

10. The apparatus of claim 6, wherein generating the parsed lab report data comprises:

determining, based at least in part on the scan results corresponding to the first set of one or more relevant portions of the lab report, structured word sequences corresponding to the one or more relevant portions of the lab report, wherein the parsed lab report data comprises the structured word sequences.

11. A non-transitory computer-readable storage medium for extracting patient data and lab result data from parsed lab report data, the computer-readable storage medium storing program code instructions that, when executed, cause a computing device to:

receive an electronic file, wherein (a) the electronic file (i) comprises a lab report and (ii) identifies a two-dimensional array of pixels, and (b) the lab report is categorized as an unknown type of lab report;

automatically identify one or more recognizable characteristics of the lab report, wherein the one or more recognizable characteristics are selected from the group consisting of a logo, text, white space, and an arrangement of text;

automatically categorize, based at least in part on the identified one or more recognizable characteristics, the lab report as a known type of lab report;

responsive to automatically categorizing the lab report as the known type of lab report, retrieve, from a template database, a template corresponding to the known type of lab report, wherein the template identifies (a) a first set of one or more pixel regions in the two-dimensional array of pixels, the first set of one or more pixel regions associated with a first set of one or more relevant portions of the lab report comprising patient data, and (b) a second set of one or more pixel regions in the two-dimensional array of pixels, the second set of one or more pixel regions associated with a second set of one or more relevant portions of the lab report comprising lab result data; and after retrieving the template:

identify, based at least in part on the template, the first set of one or more pixel regions and the second set of one or more pixel regions, wherein (a) the first set of one or more pixel regions comprises the patient data and (b) the second set of one or more pixel regions comprises the lab result data, parse, based at least in part on the template, (a) only the first set of one or more pixel regions and (b) only the second the second set of one or more pixel regions to generate parsed lab report data from the identified first set of one or more pixel regions and the identified second set of one or more pixel regions by applying one or more optical character recognition techniques, and extract the patient data and the lab result data from the parsed lab report data.

12. The computer-readable storage medium of claim 11, wherein the program code instructions, when executed, cause the computing device to automatically categorize the lab report comprises identifying at least one of a source of the lab report.

13. The computer-readable storage medium of claim 11, wherein the program code instructions, when executed, cause the computing device to identify the recognizable characteristics of the lab report using a neural net.

14. The computer-readable storage medium of claim 13, wherein the neural net comprises a restricted Boltzmann machine.

15. The computer-readable storage medium of claim 11, wherein the program code instructions, when executed, cause the computing device to generate parsed lab report data by:

determining, based at least in part on the scan results corresponding to the first set of one or more relevant portions of the lab report, structured word sequences corresponding to the one or more relevant portions of the lab report, wherein the parsed lab report data comprises the structured word sequences.

* * * * *